United States Patent
Ntziachristos et al.

(10) Patent No.: US 11,193,886 B2
(45) Date of Patent: Dec. 7, 2021

(54) DEVICE AND METHOD FOR MID-INFRARED MICROSCOPY AND ANALYSIS

(71) Applicant: Helmholtz Zentrum München Deutsches Forschungszentrum für Gesundheit und Umwelt (GMBH), Neuherberg (DE)

(72) Inventors: Vasilis Ntziachristos, Munich (DE); Miguel Angel Pleitez Rafael, Munich (DE)

(73) Assignee: Helmholtz Zentrum Munchen Deutsches Forschungszentrum Fur Gesundheit und Umwelt (GmbH)

(*) Notice: Subject to any disclaimer, the term of this patent is extended or adjusted under 35 U.S.C. 154(b) by 0 days.

(21) Appl. No.: 16/966,413

(22) PCT Filed: Jan. 30, 2019

(86) PCT No.: PCT/EP2019/052232
§ 371 (c)(1),
(2) Date: Jul. 30, 2020

(87) PCT Pub. No.: WO2019/149744
PCT Pub. Date: Aug. 8, 2019

(65) Prior Publication Data
US 2020/0355604 A1    Nov. 12, 2020

(30) Foreign Application Priority Data
Feb. 2, 2018 (EP) .................................. 18154822

(51) Int. Cl.
*G01N 21/359* (2014.01)
*G01N 21/17* (2006.01)
(Continued)

(52) U.S. Cl.
CPC ....... *G01N 21/359* (2013.01); *G01N 21/1702* (2013.01); *G01N 29/036* (2013.01);
(Continued)

(58) Field of Classification Search
CPC .. G01N 21/359; G01N 29/036; G01N 29/265; G01N 29/2425; G01N 21/1702;
(Continued)

(56) References Cited

U.S. PATENT DOCUMENTS 4,255,971 A * 3/1981 Rosencwaig ...... G01N 21/1702
356/432
6,294,764 B1 * 9/2001 Lindner .................. F23G 5/085
110/250
(Continued)

FOREIGN PATENT DOCUMENTS

JP    2013181866    9/2013

OTHER PUBLICATIONS

Tam, Andrew C. "Applications of photoacoustic sensing techniques." Reviews of Modern Physics 58.2 (1986): 381. (Year: 1986).*
(Continued)

*Primary Examiner* — Dominic J Bologna
(74) *Attorney, Agent, or Firm* — Stoel Rives LLP

(57) ABSTRACT

The invention relates to a device (1) and a corresponding method for mid-infrared microscopy and/or analysis, the device (1) comprising at least one radiation unit (10) configured to generate radiation (11) of time-varying intensity, the radiation (11) comprising one or more wavelengths in the mid-infrared spectral range, at least one refractive and/or reflective optical unit (12) which is configured to focus and/or direct the radiation (11) to at least one region or point of interest (20) located on and/or with-in an object (2), at least one detection unit (18) configured to detect ultrasound (Continued)

waves (17) emitted by the object (2) at the at least one region or point of interest (20) in response to an interaction of the radiation (11) with the object (2) and to generate according detection signals, and an evaluation unit (25) configured to derive infor-mation regarding at least one property of the object (2) from the detection signals and/or to generate a spatial and/or spatio-temporal distribution of the detection sig-nals or of information derived from the detection signals obtained for the at least one region or point of interest (20) located on and/or within the object (2).

16 Claims, 2 Drawing Sheets

(51) Int. Cl.
| | |
|---|---|
| *G01N 29/06* | (2006.01) |
| *G01N 29/265* | (2006.01) |
| *G01N 29/24* | (2006.01) |
| *G01N 29/036* | (2006.01) |
| *A61B 5/00* | (2006.01) |
| *G01N 21/64* | (2006.01) |

(52) U.S. Cl.
CPC ..... *G01N 29/0681* (2013.01); *G01N 29/2425* (2013.01); *G01N 29/265* (2013.01); *A61B 5/0077* (2013.01); *A61B 5/0095* (2013.01); *G01N 21/6458* (2013.01); *G01N 29/2418* (2013.01); *G01N 2021/1706* (2013.01); *G01N 2021/1736* (2013.01); *G01N 2021/1738* (2013.01)

(58) Field of Classification Search
CPC ....... G01N 29/0681; G01N 2021/1738; G01N 2021/1736; G01N 21/6458; G01N 29/2418; G01N 2021/1706; A61B 5/0077; A61B 5/0095

See application file for complete search history.

(56) References Cited

U.S. PATENT DOCUMENTS

2016/0235305 A1 8/2016 Wang et al.
2017/0356884 A1* 12/2017 Hu ......................... G01N 29/28

OTHER PUBLICATIONS

Buma, Takashi, Benjamin C. Wilkinson, and Timothy C. Sheehan. "Near-infrared spectroscopic photoacoustic microscopy using a multi-color fiber laser source." Biomedical optics express 6.8 (2015): 2819-2829. (Year: 2015).*
Buma, et al.,Near-Infrared Spectroscopic Photoacoustic Microscopy Using a Multi-Color Fiber Laser Source, Biomedical Optics Express, vol. 6 No. 8 ,Aug. 2015.
Hai, et al.,Near-Infrared Optical-Resolution Photoacoustic Microscopy, Optics Letters, vol. 39 No. 17 ,Sep. 1, 2014.
Tam, et al.,Applications of Photoacoustic Sensing Techniques, IBM Almaden Research Center, San Jose, CA 95120; Reviews of Modern Physics, vol. 56 No. 2 ,Apr. 1986.

* cited by examiner

DEVICE AND METHOD FOR MID-INFRARED MICROSCOPY AND ANALYSIS

BACKGROUND

N/A.

SUMMARY

The present invention relates to a device and method for mid-infrared microscopy and/or analysis.

One of the most promising label-free chemical imaging techniques is mid-infrared (mid-IR) micro-spectroscopy. Just like in the Raman-scattering approach, the mid-IR spectrum of a biomolecule depends on its spatial atomic configuration, strength of its chemical bonds, isotopic content, surrounding and/or attached molecules, hence its specificity. However, unlike Raman-scattering, in mid-IR micro-spectroscopy the endogenous contrast is provided by direct absorption of infrared light that excites vibrational-state transitions in a molecule. Additionally, due to the strong absorption coefficients of biomolecules in the mid-IR spectral region (six orders of magnitude stronger that Raman scattering) mid-IR imaging requires less light fluence than Raman imaging resulting in a lower risk of photo damage, negligible non-linear effects, and a stronger contrast. Mid-IR imaging have reached the clinical translation stage for spectro-histopathology; a field that promises quantitative cancer diagnosis using the standard histological tissue samples without mayor perturbation to the routine workflow of the pathologists.

However, despite the advantages of mid-IR imaging over Raman imaging, it has not been possible to apply mid-IR microscopy to in vivo or fresh biological tissues. A reason for this is the detection scheme used in mid-IR micro-spectroscopy. Transmission mode Fourier-Transform Infrared (FTIR) micro-spectroscopy, the most spread mid-IR imaging technique, requires thin dry tissue samples, ca. 5 µm, for mid-IR light to be able to cross the tissue and reach the optical detector. Attenuated-Total-Reflectance FTIR overcomes this limitation and is able to measure thick/opaque samples, but the penetration depth of the evanescent wave only allows obtaining information from the first 3 to 5 µm inside the sample.

It is an object of the invention to provide an improved device and method for mid-infrared microscopy and/or analysis.

According to a preferred aspect of the invention, a device for mid-infrared microscopy and/or analysis comprises: at least one radiation unit configured to generate radiation of time-varying intensity, the radiation comprising one or more wavelengths in the mid-infrared spectral range, at least one refractive and/or reflective optical unit which is configured to focus and/or direct the radiation to at least one region or point of interest located on and/or within an object, at least one detection unit configured to detect ultrasound waves emitted by the object at the at least one region or point of interest in response to an interaction of the radiation with the object and to generate according detection signals, and an evaluation unit configured to derive information regarding at least one property of the object from the detection signals and/or to generate a spatial and/or spatio-temporal distribution of the detection signals or of information derived from the detection signals obtained for the at least one region or point of interest located on and/or within the object.

According to another preferred aspect of the invention, a method for mid-infrared microscopy and/or analysis comprises the following steps: generating radiation of time-varying intensity, the radiation comprising one or more wavelengths in the mid-infrared spectral range; focusing or directing the radiation to at least one region or point of interest located on and/or within the object; detecting ultrasound waves emitted by the object at the at least one region or point of interest in response to an interaction of the radiation with the object and generating according detection signals; and deriving information regarding at least one property of the object from the detection signals and/or generating a spatial and/or spatio-temporal distribution of the detection signals or of information derived from the detection signals obtained for the at least one region or point of interest located on and/or within the object.

Preferred aspects of the invention are based on the approach to focus and/or direct mid-infrared (mid-IR) radiation of time-varying intensity, e.g. pulsed mid-infrared radiation, to an object and to detect ultrasound waves emitted by the object in response to an interaction of the radiation with the object, i.e. an absorption of radiation by the object and a subsequent temporary thermal expansion of the irradiated point or region of the object (photoacoustic effect), and to generate according detection signals. Information regarding properties of the object, e.g. the presence, content or concentration of molecules, in particular biomolecule(s), is derived from the detection signals. Alternatively or additionally, a spatial distribution, e.g. an image, and/or a spatio-temporal distribution, e.g. a series of images over time, of the detection signals or of information derived therefrom is or are generated. Preferably, depending on the wavelength(s) in the mid-IR spectral range contained in the radiation, vibrational transitions of biomolecule(s) in the object can be excited specifically, so that the corresponding acoustic waves contain information regarding the presence, content or concentration of the biomolecule(s) in the object. Contrary to optical detection, the photoacoustic sensing rescales the detection scheme from a detection of photons to a detection of acoustic, in particular ultrasound, waves produced in the object in response to absorption of the radiation according to the photoacoustic effect. Since acoustic waves are far less attenuated and scattered than photons, deeper penetrations can be achieved in photoacoustic imaging. As a result, the device and method are configured for infrared, in particular mid-IR, optoacoustic or photoacoustic microscopy and overcome limitations of the prior art. In particular, the device and method allow for in vivo label-free imaging and/or analysis of biological tissues.

In summary, the invention provides an improved device and method for mid-infrared microscopy and/or analysis.

Within the context of the invention, the terms "optoacoustic" and "photoacoustic" are used synonymously.

Within the context of the invention, the mid-infrared spectral range preferably covers wavelengths from approx. 3 µm to approx. 1 mm, preferably wavelengths from 3 to 16 µm, in particular from 3 to 12 µm.

Preferably, the object is a biological tissue and/or comprises biological cell(s), and the mid-Infrared spectral range preferably covers one or more wavelengths or wavebands which are suited to trigger specific molecular vibrational transitions of biomolecules contained in the biological tissue.

For example, information regarding at least one property of the object relates to absorption of radiation in the object, also referred to as optical absorption, and/or a concentration of one or more chromophores and/or molecules, in particular biomolecules, in the object. Preferably, the term "chromophore" relates to any kind of substances, e.g. molecules, in particular biomolecules, in the object which absorb at least a part of the radiation generated by the radiation unit.

For example, the information regarding the at least one property of the object may be derived for a single location on or in the object, for a few or a plurality of locations on or in the object and/or may relate to a two- or three-dimensional map or image representative of optical absorption and/or presence and/or concentration of chromophore(s) and/or biomolecule(s) in the object.

For example, the information regarding the at least one property of the object relates to a two- or three-dimensional optoacoustic microscopy image representing a spatial or spatio-temporal distribution of information regarding the at least one property of the object or information regarding the detection signals. Preferably, the optoacoustic microscopy image comprises a plurality of pixels exhibiting greyscale and/or color scale values.

Preferably, the obtained information regarding at least one property of the object and/or spatial and/or spatio-temporal distribution of the detection signals or of information derived from the detection signals, in particular one or more optoacoustic microscopy images, may serve as a basis for a diagnosis, in particular a medical diagnosis, and/or be used for purposes of molecular diagnostics.

In a preferred embodiment, the optical unit comprises a first cavity having a first aperture and a second aperture and being arranged such that the radiation enters the first cavity via the first aperture and ultrasound waves emitted by the object enter the first cavity via the second aperture. The optical unit further comprises at least one reflective element provided in the first cavity or forming the first cavity and configured to reflect and focus and/or direct the radiation entering the first cavity via the first aperture to the at least one region or point of interest, whereby the radiation exits the first cavity via the second aperture. Further, the detection unit is arranged to detect the ultrasound waves entering the first cavity via the second aperture. In this embodiment, the first cavity serves both as a reflector which focuses or directs the radiation toward the object and as a collector which collects ultrasound waves emitted by the object in response to the irradiation, wherein the radiation exits and the ultrasound waves enter the first cavity via the second aperture located in proximity of the object. In this way, optoacoustic microscopy is implemented in a so-called reflection mode by compact and simple design ensuring reliable irradiation of the object and detection of ultrasound waves.

Preferably, the detection unit comprises a second cavity which is acoustically coupled to the first aperture and arranged such that the radiation can pass the second cavity to enter the first cavity via the first aperture. The detection unit further comprises an ultrasound detector which is acoustically coupled to the second cavity and configured to detect ultrasound waves. In this embodiment, ultrasound waves entering the first cavity via the second aperture of the first cavity enter the second cavity via the first aperture of the first cavity and are detected by the ultrasound detector coupled to the second cavity, which further ensures and/or enhances the compactness and simplicity of the design and reliability of irradiation and ultrasound detection.

Preferably, the first cavity is an acoustically resonant cavity having one or more first cavity acoustic resonance frequencies. Alternatively or additionally, it is preferred that the second cavity is an acoustically resonant cavity having one or more second cavity acoustic resonance frequencies. Further, it is preferred that the first cavity and/or the at least one reflective element provided in the first cavity, and the second cavity form together an acoustically resonant third cavity having one or more third cavity acoustic resonance frequencies. In the aforementioned embodiments, the first and/or second and/or third cavity is an acoustically resonant cavity having one or more first, second or third cavity, respectively, acoustic resonance frequencies at which the first and/or second and/or third cavity resonates, i.e. amplifies ultrasound waves entering the first, second or third cavity, respectively, at the respective acoustic resonance frequencies and attenuates ultrasound waves at different frequencies. By designing the first and/or second and/or third cavity, e.g. by selecting size, shape and/or material of the respective cavity, the detection unit can be made particularly sensitive to desired ultrasound wavelengths or frequencies, which further enhances the reliability of ultrasound detection without adversely affecting compactness and simplicity of the overall design.

According to another preferred embodiment, the radiation unit is configured to generate pulsed radiation exhibiting a pulse repetition rate and/or radiation exhibiting an intensity oscillating with a modulation frequency, wherein the pulse repetition rate and/or the modulation frequency corresponds to at least one of the first and/or second and/or third cavity acoustic resonance frequencies. In this way, it is ensured that only or mainly those ultrasound waves are detected which are generated in the object due to the interaction between the radiation and the object, while acoustic waves which are generated due to other mechanisms are suppressed or at least attenuated. This also further enhances the reliability of ultrasound detection without adversely affecting compactness and simplicity of the overall design.

It is further preferred that the first cavity, in particular the second aperture of the first cavity, is spaced from the object to ensure a contactless optical and acoustic coupling of the first cavity to the object.

According to another preferred embodiment, the device further comprises a holder configured to hold the object, wherein the optical unit is arranged such that the radiation impinges on a first side of the object when the object is held by the holder, and the detection unit is arranged to detect ultrasound waves emitted from a second side of the object when the object is held by the holder, wherein the first and the second side of the object are opposing sides of the object. In this way, optoacoustic microscopy is implemented in a so-called transmission mode by simple and robust design ensuring both reliable irradiation of the object and detection of ultrasound waves.

Alternatively or additionally, the device preferably comprises an acoustic transmission medium and a container configured to accommodate the acoustic transmission medium, wherein the container comprises at least one container wall, in particular a bottom wall and/or a side wall, wherein the container wall comprises a window section which is transparent in the mid-infrared spectral range and configured to accommodate, in particular to carry and/or support, the object which is immersed in the acoustic transmission medium, the optical unit is arranged such that the radiation is transmitted from outside of the container through the window section and focused and/or directed to the at least one region or point of interest on or within the object being accommodated by the window section, and the detection unit is at least partially immersed in the acoustic transmission medium and configured to detect ultrasound waves emitted by the object at the at least one region or point of interest in response to an interaction of the radiation with the object. Likewise, this embodiment allows for implementing optoacoustic microscopy in a transmission mode by simple and robust design which ensures particularly reliable irradiation of the object and detection of ultrasound waves.

Preferably, the detection unit exhibits at least one sensing region or sensing point and is arranged such that the at least one sensing region or sensing point coincides or overlaps with the at least one region or point of interest irradiated with the irradiation. Preferably, the detection unit is sensitive to ultrasound waves being present within the sensing region or at the sensing point. Preferably, the detection unit comprises at least one focused ultrasound detector exhibiting a focus region or focus point, within or at which the sensitivity of the detector to ultrasound waves is maximal or exhibits at least a local maximum. In this embodiment, the sensing region or sensing point of the detection unit corresponds to the focus region or focus point, respectively, of the focused ultrasound detector. Alternatively, the detection unit comprises at least one unfocused ultrasound detector exhibiting a non-focused, e.g. a fanned, cylindrical or pencil-like, sensing region within which the detector is sensitive to ultrasound waves.

According to yet another preferred embodiment, the device comprises a temperature control unit configured to keep the temperature of the object and/or the acoustic transmission medium at a temperature value or temperature range at which the thermal expansion coefficient of at least one component of the object, in particular water contained in the object, and/or the acoustic transmission medium is zero and/or small and/or minimized, so that the generation of ultrasound waves in response to the interaction of the radiation with the at least one component of the object and/or acoustic transmission medium is avoided or reduced.

For example, the temperature control unit is configured to adjust the temperature of the holder holding the object and/or the temperature of the container accommodating the acoustic coupling medium such that the temperature of the object and/or the acoustic transmission medium is brought and/or kept at a temperature value or temperature range at which the thermal expansion coefficient of the at least one component of the object and/or the acoustic transmission medium is zero and/or small and/or minimized.

Alternatively or additionally, the temperature control unit is configured to bring and/or keep the object and/or the acoustic coupling medium to or at a temperature at which the photoacoustic effect in certain component(s) contained the object, in particular water, and/or in the coupling medium is negligible or even disappears.

Preferably, the temperature control unit is configured to adjust or keep the object and/or the coupling medium at a temperature at which at least one of the following thermodynamic parameters is zero, small or exhibits a local minimum: volumetric expansion coefficient and/or speed of sound.

For instance, the volumetric expansion coefficient of water at 4° C. is zero. By keeping the temperature of the object, e.g. biological tissue consisting 60 to 80% of water, and the coupling medium, e.g. water or water-based gel, then an undesired interference of acoustic waves generated in the water with acoustic waves of interest, i.e. ultrasound waves generated e.g. by specific biomolecule(s), can be avoided or at least reduced considerably.

In this way, the specificity and signal quality can be enhanced significantly, in some cases by orders of magnitude.

Alternatively or additionally, according to yet another preferred embodiment, the device comprises a temperature control unit configured to modulate the temperature of the object and/or the acoustic transmission medium around a temperature value or temperature range at which the thermal expansion coefficient of at least one component of the object, in particular water contained in the object, and/or the acoustic transmission medium is oscillating around zero or around another value so that the generation of ultrasound waves in response to the interaction of the radiation with the at least one component of the object and/or acoustic transmission medium can be distinguished from the substance of interest or the rest of substances composing the object.

For example, the temperature control unit is configured to modulate the temperature of the holder holding the object and/or the temperature of the container accommodating the acoustic coupling medium such that the temperature of the object and/or the acoustic transmission medium is brought to oscillate around a temperature value or temperature range at which the thermal expansion coefficient of the at least one component of the object and/or the acoustic transmission medium is oscillating around zero or around another value.

Alternatively or additionally, the temperature control unit is configured to bring and/or keep the object and/or the acoustic coupling medium to oscillate around a temperature at which the photoacoustic effect in certain component(s) contained the object, in particular water, and/or in the coupling medium is or can be distinguished from the rest.

Preferably, the temperature control unit is configured to adjust or keep the object and/or the coupling medium oscillating around a temperature at which at least one of the following thermodynamic parameters is zero, small or exhibits a local minimum: volumetric expansion coefficient and/or speed of sound.

For instance, the volumetric expansion coefficient of water at 4° C. is zero. By modulating the temperature of the object, e.g. biological tissue consisting 60 to 80% of water, and the coupling medium, e.g. water or water-based gel, then an undesired interference of acoustic waves generated in the water with acoustic waves of interest, i.e. ultrasound waves generated e.g. by specific biomolecule(s), can be filtered out and/or distinguished from the rest.

Likewise, in this way, the specificity and signal quality can be enhanced significantly, in some cases by orders of magnitude.

BRIEF DESCRIPTION OF THE DRAWINGS

Further advantages, features and examples of the present invention will be apparent from the following description of following figures.

DETAILED DESCRIPTION

Figure 1:
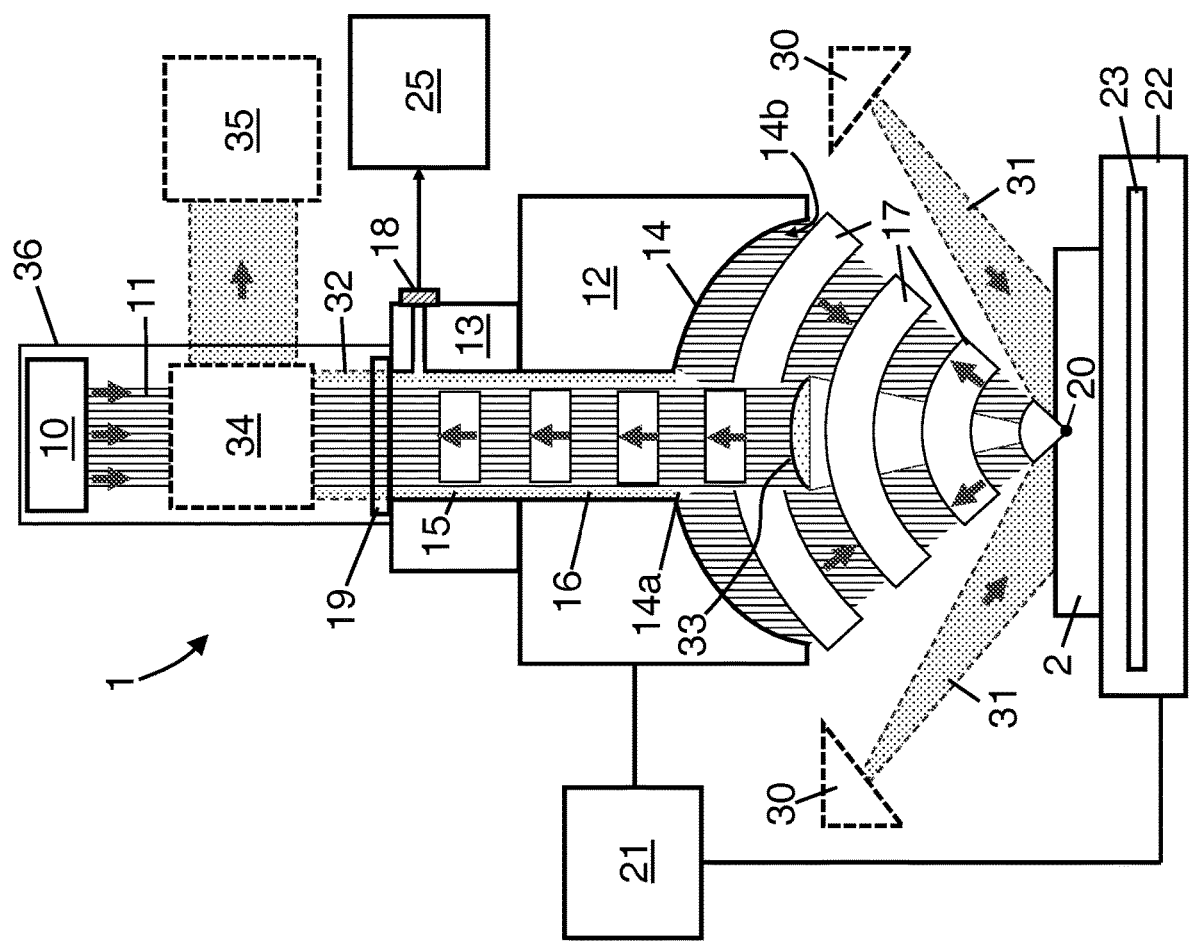
FIG. 1 shows a cross-sectional view of first example of a device for reflection-mode mid-infrared optoacoustic microscopy.

FIG. 1 shows a cross-sectional view of a first example of a device 1 for reflection-mode mid-infrared optoacoustic microscopy and/or analysis comprising a radiation unit 10 which generates electromagnetic radiation 11 having a time-varying intensity. Preferably, the radiation 11 is mid-infrared radiation and/or comprises one or more wavelengths or wavebands in the mid-infrared spectral range. Further, it is preferred that the radiation unit 10 is configured to emit pulses of radiation. For example the radiation unit 10 comprises a laser source which emits pulsed radiation in the IR or mid-IR spectral range.

The device 1 further comprises a first body 12 in which a first cavity 14 is provided, and a second body 13 in which a second cavity 15 is provided. The first cavity 14 has a distal aperture 14a, which is also referred to as first aperture, and a proximal aperture 14b, which is also referred to as second aperture. The second aperture 14b is larger than the first aperture 14a.

The radiation 11 passes a mid-infrared window 19 and the second cavity 15 and enters the first cavity 14 via the first aperture 14a. In present example, the radiation 11 impinges on a reflective element 33, e.g. a convex mirror, provided in the first cavity 14 and is reflected towards the, preferably concave, surface of the first cavity 14 which is configured to again reflect the radiation 11 such that the radiation is directed, in particular focused, towards an object 2 under investigation, in particular a biological tissue, which is located on and/or held by a holder 22. Therefore, the body 12 including the first cavity 14 and/or the curved reflective surface is also referred to as "optical unit".

Preferably, the first cavity 14 is given by or comprises a concave mirror. Further, it is preferred that the radiation 11 is focused to a focus point 20 located on or within the object 2, in particular within a point or region of interest of the object 2. Alternatively, the radiation 11 may be focused to a focus line. The focus point 20 or line may also be located at the surface of the object 2. Alternatively, the radiation 11 does not necessarily have to be focused to a point or line, but can simply be directed towards a region of any desired shape on or within the object 2.

Preferably, the device 1 further comprises a mechanism 21 which is configured to move the focus point 20, focus line or region and the object 2 relative to each other, e.g. by moving the holder 22 relative to the (fixed) device 1, moving the device 1 relative to the (fixed) holder 2, and/or moving the radiation beam 11 so that the focal point 20 moves relative to the object 2. The relative movement can be a translational and/or rotational movement in lateral (parallel to the surface of the object 2) and/or transversal (perpendicular to the surface of the object 2) direction.

The time-varying radiation 11 is at least partially absorbed by the object 2, whereupon the irradiated part of the object 2 undergoes an alternating thermal expansion and contraction resulting in an emission of acoustic waves 17. The frequency of the emitted acoustic waves 17 depends on an intensity modulation frequency and/or a pulse repetition rate of the time-varying intensity of the radiation 11. Preferably, the intensity modulation frequency and/or a pulse repetition rate is or are chosen such that the acoustic waves 17 are ultrasound waves.

At least a part of the acoustic waves 17 enters the first cavity 14 via proximal second aperture 14b. Preferably, the second cavity 14, in particular the curved surface or concave mirror forming the curved surface, is configured to collect ultrasound waves emitted by a region or point of interest on or within the object 2.

The collected ultrasound waves 17 exit the first cavity 14 via distal first aperture 14a and reach the second cavity 15 to which an ultrasound detector 18 is acoustically coupled.

Preferably, the first cavity 14 and the second cavity 15, including at least one additional optional cavity like an acoustic passage section 16 between the first cavity 14 and the second cavity 15, altogether form an acoustically resonant cavity, also referred to as third cavity 14 to 16, exhibiting one or more third cavity acoustic resonance frequencies. In this way, components of the emitted and collected acoustic waves 17 having frequencies at or around the one or more third cavity acoustic resonance frequencies are amplified, while components of the acoustic waves 17 having frequencies which are different to the one or more third cavity acoustic resonance frequencies are attenuated or even suppressed, so that the ultrasound detector 18 detects high-intensity ultrasound waves 17 at the one or more third cavity acoustic resonance frequencies.

Preferably, the radiation 11 emitted by the radiation unit 10 is pulsed radiation exhibiting a pulse repetition rate and/or radiation exhibiting an intensity oscillating with an intensity modulation frequency, wherein the pulse repetition rate and/or intensity modulation frequency corresponds to at least one of the one or more third cavity acoustic resonance frequencies. In this way, stimulation and detection of ultrasound waves 17 are synchronized with each other, whereby it is ensured that the ultrasound detector 18 detects only or predominantly ultrasound waves 17 which are stimulated by the radiation 11, whereas a detection of possible acoustic waves originating from other sources or mechanisms is avoided or at least reduced considerably.

Alternatively or additionally, depending on the particular design of the first cavity 14, second cavity 15 and/or passage section 16, it is also possible to detect high-intensity ultrasound waves 17 at one or more further resonance frequencies. For example, in case that only the first cavity 14 or the second cavity 15 is acoustically resonant (in the relevant acoustic wavelength range), high-intensity ultrasound waves 17 are detected at one or more first cavity acoustic resonance frequencies or second cavity acoustic resonance frequencies, respectively. Same applies accordingly to the passage section 16. In these embodiments, the pulse repetition rate and/or intensity modulation frequency preferably corresponds to at least one of the one or more first or second cavity or passage section 16 acoustic resonance frequencies, whereby it is ensured that the ultrasound detector 18 only or predominantly detects ultrasound waves 17 which are stimulated by the radiation 11, while possible acoustic waves originating from other sources or mechanisms are suppressed or attenuated.

Preferably, a temperature control unit 23 is provided which is configured to heat and/or cool the holder 22 and the object 2 thereon in order to keep and/or modulate the temperature of the object 2 at or around, respectively, temperature values at which the photoacoustic effect caused by specific components of the object 2, in particular water contained in the object 2, is suppressed and/or distinguished and/or separated compared to usual static ambient temperatures, e.g. around 20° C. For example, in order to suppress or reduce the photoacoustic effect caused by interaction of the radiation 11 with water in the object 2, the temperature of the object 2 is modulated around 4° C., where the thermal or volumetric expansion coefficient of water is zero or approximately zero, respectively. As a result, volume expansion and contraction due to a temporary heating of the water component by pulsed radiation 11 is oscillating around zero or another value and, therefore, considerably easier to separate and/or filter from other components than at static ambient temperatures, so that no ultrasound waves generated by the water component of the object 2 are encoded with the frequency of temperature modulation. By thermal encoding and filtering of the acoustic waves due to water in the object 2 it is possible to suppress these acoustic waves. In this way, acoustic waves generated by other components of the object 2, in particular biomolecules, can be detected with considerably higher sensitivity and specificity.

The device 1 further comprises an evaluation unit 25 which is configured to process detection signals generated by the ultrasound detector 18 when detecting the ultrasound waves 17. Preferably, the evaluation unit 25 derives information from the detection signals regarding at least one property of the object 2, e.g. an optical absorption and/or a concentration of one or more chromophores and/or biomolecules in the object 2. Alternatively or additionally, the evaluation unit 25 generates one or more images corresponding to a spatial and/or spatio-temporal distribution of the detection signals or of the information derived from the detection signals obtained for a plurality of different lateral and/or transversal locations on or within the object 2.

In summary, a particularly preferred and advantageous aspect of the first example of the device 1 for reflection-mode optoacoustic microscopy is a resonant contactless optoacoustic coupler 12 to 16, abbreviated by "OAC", which simultaneously focuses the mid-IR radiation 11 and collects and acoustically amplifies the ultrasound waves 17 to be detected by ultrasound detector 18 coupled to the acoustically resonant second cavity 15, wherein the laser repetition rate is preferably set to one of the resonant modes of the contactless OAC. In this context, the term "contactless" refers to a preferred embodiment in which, as shown in FIG. 1, the OAC 12 to 16, in particular the second aperture 14b of the first cavity 14, is provided at a finite distance from the object 2 and, therefore, does not contact or touch the object 2 during optoacoustic signal acquisition.

The first example of the device 1 described above is configured for optoacoustic microscopy. It is, however, possible to add components for optical and/or fluorescence microscopy, in particular in the visible (VIS) spectral region, in order to allow for both optoacoustic and optical, in particular VIS, and/or fluorescence microscopy.

In FIG. 1, components for (optional) optical or fluorescence microscopy are highlighted by dashed lines. Two light sources 30 generate light 31 by which the object 2 is illuminated in oblique or epi-illumination. Alternatively or additionally, a ring array of light sources (not shown) may be provided in order to obtain a particularly homogenous illumination of the object 2. Scattered and/or reflected and/or fluorescent light 32 emerging from the object 2 is collected and reflected by the concave reflective surface of the first cavity 14 towards the reflective element 33, where it is again reflected to subsequently pass the passage section 16 of the first body 12, second cavity 15 and window 19 and proceeds, via IR-VIS coupler 34, to an optical detector 35, e.g. camera, where it is detected.

Figure 2:
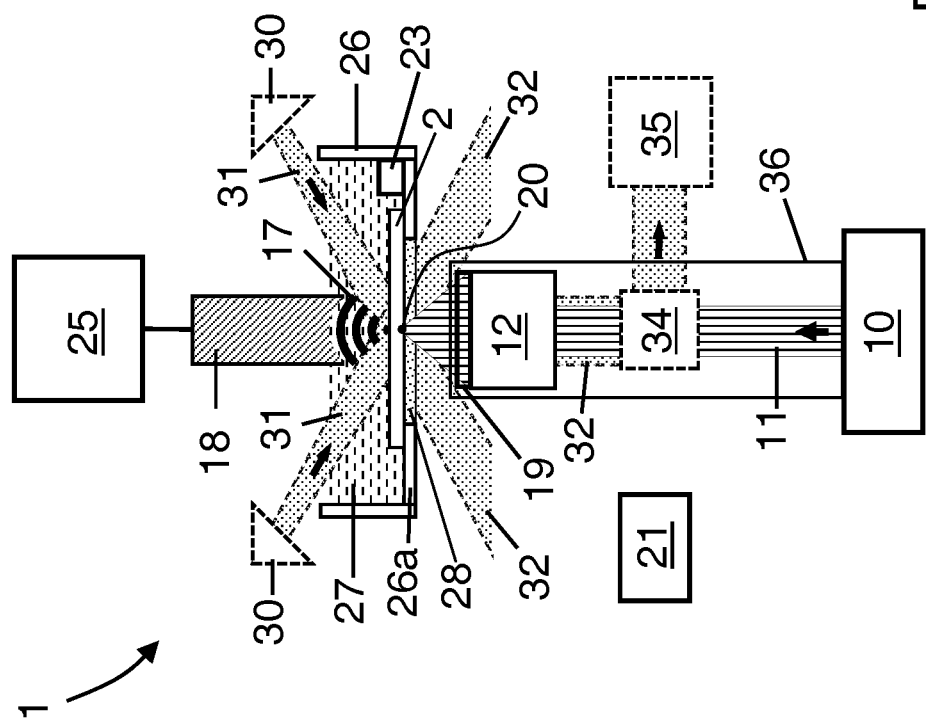
FIG. 2 shows a cross-sectional view of a second example of a device for transmission-mode mid-infrared optoacoustic microscopy.

FIG. 2 shows a cross-sectional view of a second example of a device 1 for transmission-mode mid-infrared optoacoustic microscopy and/or analysis comprising a radiation unit 10 which generates electromagnetic radiation 11 having a time-varying intensity. Preferably, the radiation 11 is mid-infrared radiation and/or comprises one or more wavelengths or wavebands in the mid-infrared spectral range. Further, it is preferred that the radiation unit 10 is configured to emit pulses of radiation 11. For example, the radiation unit 10 comprises a laser source which emits pulsed radiation 11 in the mid-IR spectral range.

The device 1 further comprises an optical unit 12 which is configured to focus and/or direct the radiation 11 to at least one region or point of interest 20 located on or within an object 2 to be investigated. For example, the optical unit 12 may comprise one or more refractive and/or reflective optical elements, e.g. curved reflective surface(s) or lens(es), respectively, which is or are preferably composed of material(s) with weak, neglectable or zero absorption and/or net change of the molecular dipole moment when interacting with mid-infrared radiation and configured to focus and/or direct the radiation 11 to the region or point of interest 20 on or within the object 2.

Further, a container 26 is configured to accommodate an acoustic transmission medium 27, e.g. water. In present example, the bottom wall 26a of the container 26 comprises a window section 28 which is transparent for the radiation 11 and configured to support and/or hold the object 2. For example, the object 2 can be enclosed in a Petri dish (not shown) which is supported and/or held by the window section 28. The object 2 and/or Petri dish enclosing the object 2 is immersed into the acoustic transmission medium 27 or is at least partially surrounded by the acoustic transmission medium 27.

The time-varying radiation 11 is at least partially absorbed by the object 2, whereupon the irradiated part of the object 2 undergoes an alternating thermal expansion and contraction resulting in an emission of acoustic waves 17. The frequency of the emitted acoustic waves 17 depends on an intensity modulation frequency and/or a pulse repetition rate of the time-varying intensity of the radiation 11. Preferably, the intensity modulation frequency and/or a pulse repetition rate is or are chosen such that the acoustic waves 17 are ultrasound waves.

At least a part of the acoustic waves 17 emitted by a region or point of interest on 20 or within the object 2 pass the acoustic transmission medium 27 above the object 2 and are detected by an ultrasound detector 18 which is at least partially immersed into the acoustic transmission medium 27. In present example, the ultrasound detector 18 is a focused detector having a focus point or a focus line which coincides with the focus line or focus point 20, respectively, of the focused radiation 11 on or within the object 2.

In present example, the optical unit 12, the window section 28 of the container 26 and the ultrasound detector 18 are arranged such that the radiation 11 impinges on a first side, in present example on the bottom side, of the object 2, whereas the generated ultrasound waves 17 are detected at a second side, in present example at the top side, of the object 2. Therefore, this arrangement is also referred to as "transmission mode".

Preferably, the bottom wall 26a and/or the window section 28 is or are configured to hold and/or support the object 2 from below while simultaneously preventing acoustic transmission medium 27 to get or enter between the object 2 and the window section 28 in order to avoid that, in addition to the object 2, also acoustic transmission medium 27, e.g. water, absorbs a part of the radiation 11 and emits acoustic waves.

Preferably, the device 1 further comprises a mechanism 21 which is configured to move the container 26, on the one hand, and the optical unit 12 and/or ultrasound detector 18, on the other hand, relative to each other in order to move the focus point 20, line or region of the radiation 11 and/or of the ultrasound transducer 18 and the object 2 relative to each other. This is accomplished, e.g., by moving the container 26 relative to the (fixed) optical unit 12 and/or (fixed) ultrasound detector 18, and/or by moving the optical unit 12 and/or ultrasound detector 18 device 1 relative to the (fixed) container 26, and/or moving the radiation beam 11 so that the focal point 20 moves relative to the object 2. The relative movement can be a translational and/or rotational movement in lateral (parallel to the surface of the object 2) and/or transversal (perpendicular to the surface of the object 2) direction.

Preferably, a temperature control unit 23 is provided which is configured to heat and/or cool the container 26 and/or the window section 26a and/or the acoustic transmission medium 27 and/or the object 2 in order to modulate the temperature of the object 2 around temperature values at which the photoacoustic effect caused by specific components of the object 2, in particular water contained in the object 2, is encoded with the temperature modulation frequency and filtered and, thereby, suppressed or at least reduced compared to other components of the objects. For example, in order to suppress or reduce the photoacoustic effect caused by interaction of the radiation 11 with water in the object 2, the temperature of the object 2 is modulated around 4° C., where the thermal or volumetric expansion coefficient of water is zero or approximately zero, respectively. As a result, volume expansion and contraction due to a temporary heating of the water component by pulsed radiation 11 is oscillating around zero or another value, and, therefore, considerably easier to separate from other components than at static temperatures, so that ultrasound waves generated by the water component of the object 2 can be filtered out. By thermal encoding and filtering of the acoustic waves due to water in the object 2 it is possible to suppress or at least reduce these acoustic waves. In this way, acoustic waves generated by other components of the object 2, in particular biomolecules, can be detected with considerably higher sensitivity and specificity.

The device 1 further comprises an evaluation unit 25 which is configured to process detection signals generated by the ultrasound detector 18 when detecting the ultrasound waves 17. Preferably, the evaluation unit 25 derives information from the detection signals regarding at least one property of the object 2, e.g. an optical absorption and/or a concentration of one or more chromophores and/or biomolecules in the object 2. Alternatively or additionally, the evaluation unit 25 generates one or more images corresponding to a spatial and/or spatio-temporal distribution of the detection signals or of the information derived from the detection signals obtained for a plurality of different lateral and/or transversal locations on or within the object 2.

Similarly to the first example shown in FIG. 1, the second example of the device 1 is configured for optoacoustic microscopy. It is, however, also possible to add components for optical and/or fluorescence microscopy, in particular in the visible (VIS) spectral region, in order to allow for both optoacoustic and optical, in particular VIS, and/or fluorescence microscopy.

In FIG. 2, components for (optional) optical or fluorescence microscopy are highlighted by dashed lines. Two light sources 30 generate light 31 by which the object 2 is illuminated in trans-illumination. Alternatively or additionally, a ring array of light sources (not shown) may be provided in order to obtain a particularly homogenous illumination of the object 2. In present example, the top side of the object 2 is illuminated with radiation 11, and at least a part of transmitted and/or fluorescent light 32 emerging from the bottom side of the object 2 is collected by the one or more refractive and/or reflective optical elements which is or are provided in the optical unit 12, and proceeds, via IR-VIS coupler 34, to an optical detector 35, e.g. camera, where it is detected.

All in all, the devices and corresponding methods described herein allow for endogenous and/or exogenous non-destructive chemical imaging and analysis of in vivo or ex-vivo biological specimens. For exogenous non-destructive chemical imaging, for instance, isotope probes using the mass effect can be used. For instance, heavier atoms to the naturally found atoms, e.g. a heavier Carbon isotope, or a Nitrile probe, can be used.

Preferably, mid-IR laser is a broadband pulsed tunable Quantum Cascade Laser. It is further preferred to provide a Mercury-Cadmium-Tellurium (MCT) detector which is used as a reference detector, and a VIS laser pointer (aligned with the IR laser) which serves as an aiming beam for easy optical adjustment.

Preferably, the mid-IR radiation beam path can be completely or partially purged by a dry inert gas, for instance dry nitrogen, contained in a chamber 36 (see FIGS. 1 and 2) where the mid-IR beam and/or optical component(s) like radiation unit 10 and/or optical unit 12 and/or window 19 and/or coupler 34, is or are at least partially enclosed. The beam path purging is preferred to remove the vibrational-rotational absorption of atmospheric CO2 and water vapor that, otherwise, may reduce the performance of the mid-IR system limiting the delivered energy and overlapping with important absorption bands of certain biomolecules.

Preferably, as indicated in FIGS. 1 and 2, the window 19 is configured to transmit the mid-IR radiation 11, on the one hand, and to keep the inert gas in the chamber 36, which is also referred to as purging unit.

Further, the reflective optics, mirrors and reflective objectives for beam modification and focusing are preferably made out of metallic surfaces such as gold or aluminum.

Further, the refractive optics, such as lenses, objectives and sample cuvettes, are preferably made out of mid-IR transparent materials such as: ZnSe, ZnS, CaF2, BaF2, Germanium, Silicon, KBr, NaCl, MgF2, Sapphire, etc.

Alternatively or additionally, the reflective optics, mirrors and reflective objectives for beam modification and focusing and/or the refractive optics, such as lenses, objectives and sample cuvettes, is or are preferably composed of material(s) with weak, neglectable or zero absorption and/or net change of the molecular dipole moment when interacting with mid-infrared radiation.

The transmission mode device shown in FIG. 2 allows for microscopy on thick tissues, about 5 mm, and cell cultures, while the reflection mode device shown in FIG. 1 using the resonant contactless OAC allows microscopy in vivo, for instance on skin. The device preferably comprises: one or more mid-IR lasers for excitation of molecular vibrations; one or more optical elements, reflective or refractive, for delivery, modification and focusing of the mid-IR radiation into the specimen, also referred to as object; one or more ultrasound sensors, resonant or not resonant, of the localized optoacoustic and/or optothermal signal generated by the laser-sample interaction; a mid-IR transparent sample cuvette; one or more elements for recovery and processing of the optoacoustic and/or optothermal signals; a sample scanning system for point-by-point image formation; and an interface for graphical display and assessment of the chemical content of a selected region or point of interest in the specimen as well as for operation and configuration of the device.

In general, a strong and specific endogenous contrast from lipids, CH bondings, and from proteins, the amide I and amide II absorption band, have been observed in the micrographs from tissues and living cell cultures. This allows to specifically separate the images according to their lipid or protein content, as it can be observed, e.g., for adipocytes and for Thymoma tumor and pancreatic tissues.

Furthermore, the sensitivity and the imaging speed of the devices make it possible to monitor metabolic process in living cells. For example, induced lipolysis on Brown and White adipocytes and the release of insulin in beta cells can be successfully monitored.

In addition to imaging of lipids and proteins, contrast from carbohydrate-related structures, glycolipids or glycoproteins, can be observed in living cell cultures. Further, nucleic acids on living cells can also be detected.

The invention claimed is:

1. A device for mid-infrared microscopy and/or analysis, the device comprising:
    at least one radiation source configured to generate radiation of time-varying intensity, the radiation comprising one or more wavelengths in the mid-infrared spectral range,
    at least one refractive and/or reflective optical unit which is configured to focus and/or direct the radiation to at least one region or point of interest located on and/or within an object,
    at least one detector configured to detect ultrasound waves emitted by the object at the at least one region or point of interest in response to an interaction of the radiation with the object and to generate according detection signals, and
    a processor configured
        to derive information regarding at least one property of the object from the detection signals and/or
        to generate a spatial and/or spatio-temporal distribution of the detection signals or of information derived from the detection signals obtained for the at least one region or point of interest located on and/or within the object;
    wherein the optical unit comprises
        a first cavity having a first aperture and a second aperture and being arranged such that the radiation enters the first cavity via the first aperture and ultrasound waves emitted by the object enter the first cavity via the second aperture, and
        at least one reflective element provided in the first cavity or forming the first cavity and configured to reflect, focus, and/or direct the radiation entering the first cavity via the first aperture to at least one region or point of interest, whereby the radiation exits the first cavity via the second aperture, wherein the detector is arranged to detect the ultrasound waves entering the first cavity via the second aperture,
    wherein the first cavity serves both as a reflector which focuses or directs the radiation toward the object and as a collector which collects ultrasound waves emitted by the object in response to the irradiation.

2. The device according to claim 1, wherein the detector comprises:
    a second cavity which is acoustically coupled to the first aperture of the first cavity and arranged such that the radiation can pass the second cavity to enter the first cavity via the first aperture, and
    an ultrasound detector which is acoustically coupled to the second cavity and configured to detect ultrasound waves.

3. The device according to claim 2, the second cavity being an acoustically resonant cavity having one or more second cavity acoustic resonance frequencies.

4. The device according to claim 2, the first cavity and/or the at least one reflective element provided in the first cavity, and the second cavity forming together an acoustically resonant third cavity having one or more third cavity acoustic resonance frequencies.

5. The device according to claim 1, the first cavity being an acoustically resonant cavity having one or more first cavity acoustic resonance frequencies.

6. The device according to claim 5, the radiation source being configured to generate pulsed radiation exhibiting a pulse repetition rate and/or radiation exhibiting an intensity oscillating with a modulation frequency, the pulse repetition rate and/or the modulation frequency corresponding to at least one of the first and/or second and/or third cavity acoustic resonance frequencies.

7. The device according to claim 1, the second aperture of the first cavity being spaced from the object to ensure a contactless optical and acoustic coupling of the first cavity to the object.

8. The device according to claim 1, further comprising a holder configured to hold the object, wherein:
    the optical unit is arranged such that the radiation impinges on a first side of the object when the object is held by the holder, and
    the detector is arranged to detect ultrasound waves emitted from a second side of the object when the object is held by the holder, wherein the first and the second side of the object are opposing sides of the object.

9. The device according to claim 1, further comprising an acoustic transmission medium and a container configured to accommodate the acoustic transmission medium, the container comprising at least one container wall comprising a bottom wall and/or a side wall, wherein:
    the container wall comprises a window section which is transparent in the mid-infrared spectral range and configured to carry and/or support the object which is immersed in the acoustic transmission medium,
    the optical unit is arranged such that the radiation is transmitted from outside of the container through the window section and focused and/or directed to the at least one region or point of interest on or within the object being accommodated by the window section, and
    the detector is at least partially immersed in the acoustic transmission medium and configured to detect ultrasound waves emitted by the object, at least one region or point of interest in response to an interaction of the radiation with the object.

10. The device according to claim 1, the detector exhibiting at least one sensing region or sensing point and being arranged such that the, at least one sensing region or sensing point coincides or overlaps with the at least one region or point of interest irradiated with the irradiation.

11. The device according to claim 1, further comprising a temperature control unit configured to keep the temperature of the object and/or the acoustic transmission medium at a temperature value or temperature range at which the thermal expansion coefficient of at least one component of the object, comprising water contained in the object, and/or the acoustic transmission medium is zero and/or small and/or minimized, so that the generation of ultrasound waves in response to the interaction of the radiation with the at least one component of the object and/or acoustic transmission medium is avoided or reduced.

12. The device according to claim 1, further comprising a temperature control unit configured to modulate the temperature of the object and/or of the acoustic transmission medium to oscillate around a temperature value or a temperature range, such that the thermal expansion coefficient of at least one component of the object comprising water contained in the object and/or of the acoustic transmission medium oscillates around zero or another value, so that ultrasound waves generated in response to the interaction of the radiation with the at least one component of the object and/or the acoustic transmission medium distinguish from ultrasound waves generated by at least another component of the object comprising a substance of interest and/or the rest of substances composing the object.

13. The device according to claim 1, further comprising a chamber accommodating an inert gas and enclosing at least a part of an optical path of the radiation and/or enclosing at least a part of one or more optical components located in the optical path of the radiation to at least partially purge the mid-IR radiation by removing vibrational-rotational absorption of atmospheric $CO_2$ and water vapor.

14. The device according to claim 13, wherein the inert gas is a dry inert gas.

15. The device according to claim 14, where the dry inert gas is dry nitrogen.

16. A method for mid-infrared microscopy and/or analysis, the method comprising the following steps:

generating radiation of time-varying intensity, the radiation comprising one or more wavelengths in the mid-infrared spectral range, focusing or directing the radiation by a first cavity to at least one region or point of interest located on and/or within the object, collecting in the first cavity ultrasound waves emitted by the object at the at least one region or point of interest in response to an interaction of the radiation with the object, detecting the ultrasound waves collected in the first cavity and generating according detection signals, and deriving information regarding at least one property of the object from the detection signals and/or generating a spatial and/or spatio-temporal distribution of the detection signals or of information derived from the detection signals obtained for at least one region or point of interest located on and/or within the object.

* * * * *